United States Patent [19]
Sekellick et al.

[11] Patent Number: 5,885,567
[45] Date of Patent: Mar. 23, 1999

[54] TREATMENT OF INFECTION IN FOWL BY ORAL ADMINISTRATION OF AVIAN INTERFERON PROTEINS

[75] Inventors: Margaret J. Sekellick; Philip I. Marcus, both of Storrs; Anthony F. Ferrandino, Bolton, all of Conn.

[73] Assignee: University of Connecticut, Storrs, Conn.

[21] Appl. No.: 308,821

[22] Filed: Sep. 19, 1994

Related U.S. Application Data

[63] Continuation-in-part of Ser. No. 235,402, Apr. 28, 1994, abandoned, which is a continuation-in-part of Ser. No. 139,909, Oct. 22, 1993, Pat. No. 5,641,656.

[51] Int. Cl.$^6$ ............................. A61K 38/21; C12N 15/20
[52] U.S. Cl. ......................... 424/85.4; 424/85.7; 424/442
[58] Field of Search .................... 424/85.4, 442, 424/499, 85.2; 435/69.51; 514/44

[56] References Cited

U.S. PATENT DOCUMENTS

| | | |
|---|---|---|
| 4,027,021 | 5/1977 | Underwood ............................. 514/231.8 |
| 4,289,690 | 9/1981 | Pestka ....................................... 530/351 |
| 4,462,985 | 7/1984 | Cummins . |
| 4,497,795 | 2/1985 | Cummins . |
| 4,820,515 | 4/1989 | Cummins . |
| 5,019,382 | 5/1991 | Cummins ................................ 424/85.4 |

FOREIGN PATENT DOCUMENTS

| | | |
|---|---|---|
| 0088622 | 9/1983 | European Pat. Off. . |
| 89/01972 | 3/1989 | WIPO . |
| 93/15185 | 8/1993 | WIPO . |
| 95/21629 | 8/1995 | WIPO . |
| 97/03688 | 2/1997 | WIPO . |
| 97/05903 | 2/1997 | WIPO . |

OTHER PUBLICATIONS

Fynan, E.F., et al. (1993) *Proc. Natl. Acad. Sci. USA* 90: 11478–82.
Guggenheim, M.A., et al. (1968) *Science* 159: 542–43.
Watson, G., et al. (1984) *Antiviral Res.*, vol. 4, special issue: Proc. ISIR Conf. on Biology of the Interferon System; p. 63, abst. No. B25.
Salter, Donald W. et al., "Transgenic Chickens: Insertion of Retroviral Genes into the Chicken Germ Line," *Virology*, 157:236–240 (1987).
Salter, Donald W. et al., "Lack of genetic transmission of avian leukosis proviral DNA in viremic Japanese quall," (Abstract) Proceedings of the Second Symposium on Genetic Engineering of Animals, Cornell University, Ithaca, NY (1989). *Journal of Reproduction and Fertility*, Supplement 41 (1990).
Fernando, Lawrence P. and Andrews Glen K., "Cloning and expression of an avian metallothionein–encoding gene," *Gene*, 81:177–183 (1989).
Marcus, Philip I. and Sekellick, Margaret J., "Interferon Induction by Viruses. XVI. 2–Aminopurine Blocks Selectively and Reversibly an Early Stage in Interferon Induction," *J. Gen. Virol.*, 69:1637–1645 (1988).

Svitlik, Charles and Marcus, Philip I., "Interferon Induction by Viruses. XII. Inhibition of Protein Synthesis Renders Aged Chick Embryo Cells Refractory to Interferon Induction," *J. Gen. Virol.*, 66:883–886 (1985).
Sekellick, Margaret J. and Marcus, Philip I., "Inferferon Induction by Viruses. XIV. Development of Interferon Inducibility and Its Inhibition in Chick Embryo Cells Aged In Vitro," *Journal of Interferon Research*, 5:651–667 (1985).
Sekellick, Margaret J. and Marcus, Philip I., "Induction of High Titer Chicken Interferon," *Methods in Enzymology*, 119:115–125 (1986).
Yoshida, Itsuroand Marcus, Philip I., "Interferon Induction by Virsuses. XX. Acid–Labile Interferon Accounts for the Antiviral Effect Induced by Poly(rI)•Poly(rC) in Primary Chick Embryo Cells," *Journal of Interferon Research*, 10:461–468 (1990).
Marcus, Philip I. et al., "Interferon Induction by Viruses. XXI. Vesicular Stomatitis Virus: Interferon Inducibility as a Phylogenetic Marker," *Jounral of Interferon Research*, 12:297–305 (1992).
Sekellick, Margaret J. et al., "Development of the Interferon System. I. In Chicken Cells Development in Ovo Continues on Time In Vitro," *In Vitro Cell. Dev. Biol.*, 26:997–1003 (1990).
Hough, S. and R.H. Foote, "The Effect of the Cornell Particle Gun on Bull and Rabbit Spermatozoa," Abstract, *Biology of Reproduction*, 42:65 (1990).
Crittenden, L.B. and Salter, D.W., "Expression and mobility of retroviral inserts in the chicken germ line," *Transgenic Models in Medicine and Agriculture*, pp. 73–87, Wiley–Liss, Inc. (1990).
Reed, M.L. et al., "Microinjection of liposome–encapsulated DNA into murine and bovine blastocysts," Abstract, *Theriogenology*, 29(1):293 (1988).
Coonrod, S.A. et al., "Successful non–surgical collection of ovine embryos," Abstract, *Theriogenology*, 25(1):149 (1986).
Shuman, R.M. et al., "Tissue specificity of a retrovirus gene transfer vector revealed by expression of a bacterial marker gene," Abstracts of the 9th Annual Meeting of The Southern Poultry Science Society, *Poultry Science*, 67, Supplement 1:156 (1988).
Shuman, R.M., "Use of retrovirus vectors for gene insertion in poultry and swine," *J. of Dairy Sci.*, 72(suppl. 1):61 (1989).

(List continued on next page.)

*Primary Examiner*—David L. Fitzgerald
*Attorney, Agent, or Firm*—Hamilton, Brook, Smith & Reynolds, P.C.

[57] ABSTRACT

The present invention relates to a chicken interferon gene coding for the amino acid sequence of SEQ ID NO: 1. The present invention also relates to a method of producing biologically active chicken interferon recombinantly, a method of isolating other non-mammalian interferon genes, a method of making a transgenic fowl having the chicken interferon gene incorporated therein, and method for delivery of the chicken interferon in the bird, such as by genetic immunization or aerosol. Expression of the chicken IFN gene yields functional chicken interferon.

18 Claims, 1 Drawing Sheet

OTHER PUBLICATIONS

Sekellick, Margaret J. et al., "Chicken Interferon Gene: Cloning, Expression, and Analysis," *Journal of Interferon Research,* 14:83–91 (1994).

Wilson, V. et al., "A Comparison of Vertebrate Interferon Gene Families Detected by Hybridization with Human Interferon DNA," *J. Mol. Biol.,* 166:457–475 (1983).

Schultz, Ulla et al., "Molecular Cloning of Duck Interferon" *J. of Interferon Research,* 14 (Suppl 1):S45 (1994).

Schultz, Ulla et al., "Purified Recombinant chicken Interferon from *E. Coli* is Biologically Active," *J. of Interferon Research,* 14 (Supple 1):S55 (1994).

Shuman, R.M., "Production of transgenic birds," *Experientia 47(9)*:897–905 (1991).

Tamai, Tadakazu et al., "Cloning and expression of flatfish (*Paralichthys olivaceus*) interferon cDNA," *Biochimica et Biophysica Acta 1174(2)*:182–186 (1993).

Sekellick, Margaret J. et al., "Chicken Interferon cDNA Probe," *Journal of Interferon Research 13,* Suppl. 1:S68, Abstract PW1–2 of The 1993 Annual Meeting of the ISICR, Tokyo, Japan (1993).

Krempien, Ursula et al., "Purification of Chick Interferon by Zinc Chelate Affinity Chromatography and Sodium Dodecylsulfate–Polyacrylamide Gel Electrophoresis," *Journal of Interferon Research 5(1)*:209–214 (1985).

Kohase, Masayoshi et al., "Purification and Characterization of Chick Interferon Induced by Viruses," *J. Gen Virol. 67(1)*:215–218 (1986).

Adolf, G.R., Monoclonal Antibodies and Enzyme Immunoassays Specific for Human Interferon(INF)ω1: Evidence that IFN–ω1 is a Component of Human Leukocyte IFN, *Virology 175*:410–417 (1990).

Beltz et al., Isolation of Multigene Families and Determination of Homologies by Filter Hybridization Methods, *Meth. Enzymol. 100*:266–285 (1983).

Bodo & Maurer–Fogy, Molecular Species of Recombinant Human Interferon Alpha 2 Detected in Affinity Purified Preparations. In: *The Biology of the Interferon System* (ed. Stewart, W.E., II Schellekens, H.), Elsevier Scientific Publishing Co., Amsterdam, pp. 59–64 (1985).

Breitling et al., Secretory expression in *Escherichia coli* and *Bacillus subtilis* of human interferon α genes directed by staphylokinase signals, *Mol. Gen. Genet. 217*:384–391 (1989).

Chang et al., Nucleotide sequence of the alkaline phosphatase gene of *Escherichia coli, Gene 44*:121–125 (1986).

Derwent World Patent Index, English language abstract of European Patent 0 115 613.

Dworkin–Rastl et al., Construction of expression plasmids producing high levels of human leukocyte–type interferon in *Escherichia coli, Gene 21*:237–248 (1983).

Fuh et al., The Human Growth Hormone Receptor, *J. Biol. Chem. 265(6)*:3111–3115 (1990).

Goeddel et al., Human leukocyte interferon produced by *E. coli* is biologically active, *Nature 287*:411–416 (1980).

Goeddel et al., The structure of eight distinct cloned human leukocyte interferon cDNAs, *Nature 290*:20–26 (1981).

Hauptmann & Swetly, A novel class of human type I interferons, *Nucl. Acid Res. 13(13)*:4739–4749 (1985).

Ho et al., Site–directed mutagenesis by overlap extension using the polymerase chain reaction, *Gene 77*:51–59 (1989).

Kafatos et al., Determination of nucleic acid sequence homologies and relative concentrations by a dot hybridization procedure, *Nucl. Acids Res. 7(6)*:1541–1552 (1979).

Lee et al., Characterization of Gene Encoding Heat–Stable Toxin II and Preliminary Molecular Epidemiological Studies of Enterotoxigenic *Escherichia coli* Heat–Stable Toxin II Producers, *Infection and Immunity 42(1)*:264–268 (1983).

Mantei et al., The nucleotide sequence of cloned human leukocyte interferon cDNA, *Gene 10*:1–10 (1980).

Owen & Pitcher, Current Methods for Estimating DNA Base Composition and Levels of DNA–DNA Hybridization, *Chemical Methods in Bacterial Systematics,* pp. 67–93 (1985).

Picken et al., Nucleotide Sequence of the Gene for Heat––Stable Enterotoxin II of *Escherichia coli, Infection and Immunity 42(1)*:269–275 (1983).

Shuttleworth et al., Sequence of the gene for alkaline phosphatase from *Escherichia coli* JM83, *Nucl. Acid Res. 14(2)*:8689 (1986).

Streuli et al., At Least Three Human Type α Interferons: Structure of α2, *Science 209*:1343–1347 (1980).

Thatcher & Panayotatos, Purification of Recombinant Human IFN–α2, *Methods Enzymol. 119*:166–177 (1986).

Twigg and Sherratt, Trans–complementable copy–number mutants of plasmid ColE1, *Nature 283*:216–218 (1980).

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 767 base pairs
        ( B ) TYPE: nucleic acid
        ( C ) STRANDEDNESS: single
        ( D ) TOPOLOGY: linear     ( i x ) FEATURE:
        ( A ) NAME/KEY: CDS
        ( B ) LOCATION: 55..633

( x i ) SEQUENCE DESCRIPTION: SEQ ID NO:1:

```
CGCACCACCA CCGAGCCCCA CCAGGCTCCT GCCCAGCACA ACGCGAGTCC CACC ATG        57
                                                              Met
                                                              1

GCT GTG CCT GCA AGC CCA CAG CAC CCA CGG GGG TAC GGC ATC CTG CTG       105
Ala Val Pro Ala Ser Pro Gln His Pro Arg Gly Tyr Gly Ile Leu Leu
              5                  10                  15

CTC ACG CTC CTT CTG AAA GCT CTC GCC ACC ACC GCC TCC GCC TGC AAC       153
Leu Thr Leu Leu Leu Lys Ala Leu Ala Thr Thr Ala Ser Ala Cys Asn
            20                  25                  30

CAC CTT CGC CCC CAG GAT GCC ACC TTC TCT CAC GAC AGC CTC CAG CTC       201
His Leu Arg Pro Gln Asp Ala Thr Phe Ser His Asp Ser Leu Gln Leu
        35                  40                  45

CTC CGG GAC ATG GCT CCC ACA CTA CCC CAG CTG TGC CCA CAG CAC AAC       249
Leu Arg Asp Met Ala Pro Thr Leu Pro Gln Leu Cys Pro Gln His Asn
50                  55                  60                  65
```

```
GCG  TCT  TGC  TCC  TTC  AAC  GAC  ACC  ATC  CTG  GAC  ACC  AGC  AAC  ACC  CGG                297
Ala  Ser  Cys  Ser  Phe  Asn  Asp  Thr  Ile  Leu  Asp  Thr  Ser  Asn  Thr  Arg
                    70                      75                      80

CAA  GCC  GAC  AAA  ACC  ACC  CAC  GAC  ATC  CTT  CAG  CAC  CTC  TTC  AAA  ATC                345
Gln  Ala  Asp  Lys  Thr  Thr  His  Asp  Ile  Leu  Gln  His  Leu  Phe  Lys  Ile
               85                           90                      95

CTC  AGC  AGC  CCC  AGC  ACT  CCA  GCC  CAC  TGG  AAC  GAC  AGC  CAA  CGC  CAA                393
Leu  Ser  Ser  Pro  Ser  Thr  Pro  Ala  His  Trp  Asn  Asp  Ser  Gln  Arg  Gln
              100                          105                 110

AGC  CTC  CTC  AAC  CGG  ATC  CAC  CGC  TAC  ACC  CAG  CAC  CTC  GAG  CAA  TGC                441
Ser  Leu  Leu  Asn  Arg  Ile  His  Arg  Tyr  Thr  Gln  His  Leu  Glu  Gln  Cys
     115                     120                     125

TTG  GAC  AGC  AGC  GAC  ACG  CGC  TCC  CGG  ACG  CGA  TGG  CCT  CGC  AAC  CTT                489
Leu  Asp  Ser  Ser  Asp  Thr  Arg  Ser  Arg  Thr  Arg  Trp  Pro  Arg  Asn  Leu
130                      135                     140                     145

CAC  CTC  ACC  ATC  AAA  AAA  CAC  TTC  AGC  TGC  CTC  CAC  ACC  TTC  CTC  CAA                537
His  Leu  Thr  Ile  Lys  Lys  His  Phe  Ser  Cys  Leu  His  Thr  Phe  Leu  Gln
                    150                          155                     160

GAC  AAC  GAT  TAC  AGC  GCC  TGC  GCC  TGG  GAA  CAC  GTC  CGC  CTG  CAA  GCT                585
Asp  Asn  Asp  Tyr  Ser  Ala  Cys  Ala  Trp  Glu  His  Val  Arg  Leu  Gln  Ala
               165                          170                     175

CGT  GCC  TGG  TTC  CTG  CAC  ATC  CAC  AAC  CTC  ACA  GGC  AAC  ACG  CGC  ACT                633
Arg  Ala  Trp  Phe  Leu  His  Ile  His  Asn  Leu  Thr  Gly  Asn  Thr  Arg  Thr
          180                          185                     190

TAGCCCCAAA  CGCACCTCCC  ACCCTTGTCC  TATTTATCTA  TTTATTCAAC  TATTTATACA                         693

AACGCCTATT  TATTCTTCTA  TTTATTCTTC  TATTTATTCA  GACAAAATAA  AGCTCTCCTT                         753

TTCAACACTG  AAAA                                                                               767

( 2 ) INFORMATION FOR SEQ ID NO:2:

( i ) SEQUENCE CHARACTERISTICS:
            ( A ) LENGTH: 162 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

Cys  Asn  His  Leu  Arg  Pro  Gln  Asp  Ala  Thr  Phe  Ser  His  Asp  Ser  Leu
  1                 5                         10                      15

Gln  Leu  Leu  Arg  Asp  Met  Ala  Pro  Thr  Leu  Pro  Gln  Leu  Cys  Pro  Gln
               20                      25                      30

His  Asn  Ala  Ser  Cys  Ser  Phe  Asn  Asp  Thr  Ile  Leu  Asp  Thr  Ser  Asn
               35                      40                      45

Thr  Arg  Gln  Ala  Asp  Lys  Thr  Thr  His  Asp  Ile  Leu  Gln  His  Leu  Phe
     50                      55                      60

Lys  Ile  Leu  Ser  Ser  Pro  Ser  Thr  Pro  Ala  His  Trp  Asn  Asp  Ser  Gln
 65                      70                      75                      80

Arg  Gln  Ser  Leu  Leu  Asn  Arg  Ile  His  Arg  Tyr  Thr  Gln  His  Leu  Glu
                    85                      90                      95

Gln  Cys  Leu  Asp  Ser  Ser  Asp  Thr  Arg  Ser  Arg  Thr  Arg  Trp  Pro  Arg
               100                     105                     110

Asn  Leu  His  Leu  Thr  Ile  Lys  Lys  His  Phe  Ser  Cys  Leu  His  Thr  Phe
          115                     120                     125

Leu  Gln  Asp  Asn  Asp  Tyr  Ser  Ala  Cys  Ala  Trp  Glu  His  Val  Arg  Leu
     130                     135                     140

Gln  Ala  Arg  Ala  Trp  Phe  Leu  His  Ile  His  Asn  Leu  Thr  Gly  Asn  Thr
145                     150                     155                     160
```

Arg Thr (2) INFORMATION FOR SEQ ID NO:3:

(i) SEQUENCE CHARACTERISTICS:
        (A) LENGTH: 269 base pairs
        (B) TYPE: nucleic acid
        (C) STRANDEDNESS: single
        (D) TOPOLOGY: linear     (ii) MOLECULE TYPE: cDNA to mRNA     (xi) SEQUENCE DESCRIPTION: SEQ ID NO:3:

```
TTGGCCATCT ATGAGATGCT CCAGCAGATT TTCAAAATCC TCAGCAGCCC CAGCACTCCA      60
GCCCACTGGA ACGACAGACG CGAACGCCAA AGCCTCCTCA CACCGGAGTC CACCGCTACA     120
CCAGACCTGA GCAATGCTTG GACAGCAGAG ACACGCTCTC CGGACGCGAT GGCCTCGCAA     180
CCTTCACCTC ACCATCAAAA AACACTTCAG CTGCCTCCAC ACCTTCCTCC AAGACAACGA     240
TTACACGCCT GCGCTTGGAC AGTGGTCCG                                       269
```

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear     (xi) SEQUENCE DESCRIPTION: SEQ ID NO:4:

```
TTGGCCATCT ATGAGATGCT CCAGMANATH TT                                    32
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO:5:

```
CGGACCACTG TCCANGCRCA                                                  20
```

(2) INFORMATION FOR SEQ ID NO:6:

(i) SEQUENCE CHARACTERISTICS:
        (A) LENGTH: 193 amino acids
        (B) TYPE: amino acid
        (D) TOPOLOGY: linear     (ii) MOLECULE TYPE: protein     (xi) SEQUENCE DESCRIPTION: SEQ ID NO:6:

```
Met Ala Val Pro Ala Ser Pro Gln His Pro Arg Gly Tyr Gly Ile Leu
 1               5                  10                  15

Leu Leu Thr Leu Leu Leu Lys Ala Leu Ala Thr Thr Ala Ser Ala Cys
                20                  25                  30

Asn His Leu Arg Pro Gln Asp Ala Thr Phe Ser His Asp Ser Leu Gln
             35                  40                  45

Leu Leu Arg Asp Met Ala Pro Thr Leu Pro Gln Leu Cys Pro Gln His
         50                  55                  60

Asn Ala Ser Cys Ser Phe Asn Asp Thr Ile Leu Asp Thr Ser Asn Thr
 65                  70                  75                  80

Arg Gln Ala Asp Lys Thr Thr His Asp Ile Leu Gln His Leu Phe Lys
                 85                  90                  95
```

| | | | | | | | | | | | | | | |
|---|---|---|---|---|---|---|---|---|---|---|---|---|---|---|
| Ile | Leu | Ser | Ser 100 | Pro | Ser | Thr | Pro | Ala 105 | His | Trp | Asn | Asp | Ser 110 | Gln | Arg |
| Gln | Ser | Leu 115 | Leu | Asn | Arg | Ile | His 120 | Arg | Tyr | Thr | Gln | His 125 | Leu | Glu | Gln |
| Cys | Leu 130 | Asp | Ser | Ser | Asp | Thr 135 | Arg | Ser | Arg | Thr | Arg 140 | Trp | Pro | Arg | Asn |
| Leu 145 | His | Leu | Thr | Ile | Lys 150 | Lys | His | Phe | Ser | Cys 155 | Leu | His | Thr | Phe | Leu 160 |
| Gln | Asp | Asn | Asp | Tyr 165 | Ser | Ala | Cys | Ala | Trp 170 | Glu | His | Val | Arg | Leu 175 | Gln |
| Ala | Arg | Ala | Trp 180 | Phe | Leu | His | Ile | His 185 | Asn | Leu | Thr | Gly | Asn 190 | Thr | Arg |
| Thr | | | | | | | | | | | | | | | |

TREATMENT OF INFECTION IN FOWL BY ORAL ADMINISTRATION OF AVIAN INTERFERON PROTEINS

RELATED APPLICATION

This application is a continuation-in-part of U.S. patent application Ser. No. 08/235,402 filed Apr. 28, 1994, now abandoned, which is a continuation-in-part of U.S. patent application Ser. No. 08/139,909, filed Oct. 22, 1993, now U.S. Pat. No. 5,641,656, the entire teachings of which are incorporated herein by reference.

GOVERNMENT SUPPORT

The invention described herein was supported in whole or in part by Grant Number AI18381 from the National Institute of Allergy and Infectious Disease. The Government has certain rights in the invention.

BACKGROUND OF THE INVENTION

Mammalian interferons are valuable proteins useful in protecting and treating animals and humans from viral and other diseases, through the myriad actions of interferon (IFN). Marcus, *Encyclopedia of Virology*, 2:733–739 (1994); Krown et al., *Encyclopedia of Virology*, 2:739–745 (1994). The Food and Drug Administration has approved several uses of human IFN. Comparable studies with chickens and other avian species have been limited by the availability of chicken and avian IFN. Induction of avian interferon by virus has been successful in primary chick embryo cells "aged" in vitro, with yields of more than 100,000 units of IFN per $10^7$ cells (Sekellick and Marcus, *Methods in Enzymology*, 119:115–125 (1986)), and chicken interferon (ChIFN) has been shown specifically to protect chicken cells against the lethal action of several viruses (Marcus and Sekellick, *Virology*, 69:378–393 (1976); Marcus et al., *Journal of General Virology*, 64:2419–1431 (1983); Portnoy and Marigan, *Journal of Infectious Diseases*, 124:545–552 (1971); Vengris and Maré, *Avian Diseases*, 17:755–767 (1973)).

Virus diseases represent a continuous threat to the poultry industry. For example, the "Foreign Animal Disease Report," USDA, 1994, reported in 1983/1984 that an outbreak of the highly pathogenic H5N2 avian influenza virus in Pennsylvania, Maryland, New Jersey and Virginia resulted in the death of 17 million birds. A less pathogenic strain was isolated on a game farm in Maryland in 1993. The infection led to the depopulation of the flock. Some important parasitic diseases of chickens like that caused by Eimeria may be controllable by interferon through its effects on the immune system. Interferon is gaining increased attention as an antiparasitic agent, (Murray, *Journal Interferon Research*, 12:319–322 (1992)).

Many factors determine how much interferon is induced by a particular virus. These factors include its origin and passage history, the host cell, incubation conditions and time, and the multiplicity of infection. Stewart, "The Interferon System", 2nd. ed., Vienna:Springer-Verlag, pp 27–57; Marcus, Sekellick and Nichol, *Journal of Interferon Research*, 12:297–305 (1992).

SUMMARY OF THE INVENTION

This invention relates to isolated genes and recombinant DNA coding for non-mammalian interferon, processes for preparing and isolating them and methods of use therefor. The isolated gene preferably codes for avian, fish or reptile interferon. Preferred embodiments of avian interferon include fowl, such as but not limited to chickens, ostrich, emus, turkeys, ducks, geese, quails and exotic birds, such as parrots, cockatoos, cockatiels, and other commercially valuable birds. The nucleotide sequences encoding chicken interferon are described herein.

This invention also relates to a method of producing recombinant interferon which comprises culturing a transformed microorganism capable of producing the recombinant interferon, said microorganism having inserted therein a recombinant interferon gene, such as the DNA sequence of SEQ ID NO: 1, (encoding chicken interferon, GenBank Accession No. U07868) and recovering said interferon. The amino acid sequence encoding the signal and mature chicken IFN protein has been deduced and is described herein (SEQ ID NO: 1). The mature chicken IFN protein has been shown to be biologically functional. The transformed microorganism employed may be any host cell or cells capable of producing the recombinant protein. Preferably the host cell is derived from a eukaryote, mammalian cell culture or prokaryote, with eukaryote (e.g., insect cells) or mammalian cell culture (e.g., CHO cells) being most preferred in order to achieve glycosylation. Active material has also been obtained from *E. coli*.

A cDNA probe is also described herein. For example, the probe can comprise the nucleotide sequence of SEQ ID NO: 3. This cDNA probe, along with the cDNA of SEQ ID NO: 1, can be used to isolate and identify other non-mammalian interferon genes, such as other avian species, fish and reptiles, due to ancestral homology. For example, a probe can comprise at least about a twenty base pair segment of the DNA sequence of SEQ ID NO: 1 which will bind to the complement of said sequence.

The invention also pertains to a plasmid comprising a) DNA sequence coding for non-mammalian interferon, preferably avian, fish and reptile interferon, most preferably chicken interferon, and b) a promoter sequence operably linked to said DNA sequence, preferably a chicken metallothionein promoter.

The novel plasmid constructs of this invention can be used to produce abundant quantities of recombinant interferon for administration to fowls and exotic birds, in order to prevent viral and/or parasitic infections. In another embodiment, interferon DNA can be introduced by genetic augmentation, i.e., genetic immunization. According to this method, DNA is introduced into the skin of the bird using a hand-held biolistic system (Sanford et al., *Technique*, 3:3–16 (1992)) and serves as a template for manufacture of interferon. Tang et al., *Nature*, 356:152–154 (1992). Alternatively, the DNA and constructs containing the DNA of this invention can be used to produce transgenic fowl. The transgenic fowl would harbor an inducible plasmid for the transient expression of chicken interferon. Such transient expression would be induced at a time in the development of the fowl which would not retard growth but would provide protection against viral and/or parasitic infections.

This invention further pertains to transgenic fowl wherein its germ cells and/or somatic cells contain the recombinant DNA comprising an isolated avian interferon DNA introduced at an embryonic stage, and a method of making the same. Preferably, the recombinant DNA is substantially endogenous to the transgenic fowl, such as that coding for chicken interferon where the transgenic fowl is a transgenic chicken. In one embodiment, a promoter sequence heterologous to the chicken promoter can be operably linked to the recombinant DNA coding for chicken interferon in order to selectively induce expression of the interferon gene. An example of a heterologous promoter is the chicken metallothionein promoter which can be regulated by providing a source of metallic ions to the fowl. By this method, it is possible to treat or prevent viral and/or parasitic infection by inducing transcription of the DNA in the transgenic fowl.

DETAILED DESCRIPTION OF THE INVENTION

The first DNA nucleotide sequence and probe therefor that codes for a non-mammalian interferon, namely chicken interferon, are described herein. The nucleotide sequence coding the complete chicken interferon gene has been determined and is set forth in SEQ ID NO: 1. The sequence is 763 nucleotides in length and 30 contains the following nucleotides starting at the 5' end: 54 bases of the 5' flanking sequence, 93 bases coding a 31 amino acid signal protein, 486 bases coding the mature chicken interferon protein, 3 bases for a stop signal, 127 bases comprising the 3' flanking region and a poly(A) tail.

The probe is the first DNA nucleotide sequence found to be specific for the chicken interferon messenger RNA (mRNA). A special system of "aged" primary chick embryo cells (Sekellick and Marcus, *Methods in Enzymology*, 119:115–125 (1985)), was used to induce the messenger RNA for chicken interferon. The chicken interferon probe, exemplified shares less than 25% nucleotide sequence identity with reported mammalian interferon α and β species.

Primers were also designed to capture and synthesize a portion of the chicken interferon gene. PCR products were then produced, using these primers to amplify sequences from messenger RNA obtained from "aged" primary chick embryo cells, according to Sekellick and Marcus, "*Methods in Enzymology*", 19:115–125, (1986). A successful Northern blot using the chicken interferon DNA probe demonstrating the size of the interferon messenger RNA was obtained. The chicken interferon DNA probe is a 269 base sequence that includes two primer regions. The Northern blot was obtained using the chicken interferon DNA probe demonstrating an inducible messenger RNA with proper size and characteristics in response to control treatments in UV-avian reovirus infected "aged" primary chick embryo cells, as well as poly I-poly C treatment, and infection with vesicular stomatitis virus (VSV) serotype Indiana (IN) #22-20, and its absence under appropriate test conditions (e.g., in the presence of cyclokeximide, actinomycin D or 2-aminopurine or infection with VSV (IN) #22-25 in the same system.

The cDNA probe obtained by this method has the nucleotide sequence of SEQ ID No: 3. The probe comprises a 269 nucleotide sequence having a 5' primer region of 32 bases, a 3' primer region of 20 bases and a 217 base partial sequence of the chicken interferon gene. The probe can be manufactured by alternative processes well known in the art. Other useful probes, as discussed above, can be made in the same or similar manner. Preferred probes include those comprising at least about a 20 base pair segment of the DNA sequence of SEQ ID NO: 1 which will bind to the complement of the interferon gene. Preferably the base pair segment will be located in the region which corresponds to about nucleotide 487 to about nucleotide 633 of SEQ ID NO: 1. A highly conserved region in mammalian interferons is found at the 547–579 segment.

The probe can then be used in screening a non-mammalian, such as an avian, particularly a chicken or duck, cDNA library, according to the methods described in detail below. For example, in this procedure with a screening in a chicken cDNA library, 5 clones containing full-length coding regions and 1 truncated clone were isolated. The mRNAs coding for chicken and duck interferon were successfully obtained. Synthesis of cDNA from mRNA coding for the interferon can be performed by methods described in detail below.

The thus obtained cDNA can be incorporated into a cloning vehicle to obtain transformants. Cloning vehicles which can be used in this invention include plasmids, such as the SuperScript Plasmid System for cDNA Synthesis and Plasmid Cloning (available from GIBCO/BRL; Life Technologies, Inc.). The CDNA thus cloned is produced with Not I and Sal I termini for directional cloning into the Not I- Sal-I-Cut plasmid pSPORT I.

Using appropriate plasmids, or cloning vehicles, the DNA can be incorporated into an appropriate cell, such as a prokaryote or eukaryote, according to methods known in the art, such as *Current Protocols in Molecular Biology*, F. Ausubel, et al., (Eds.). The transformants are cultured to thereby express the cell protein. Confirmation of the expression of chicken interferon can be achieved by known assays. The expressed chicken interferon can be isolated from the culture according to known techniques, including, for example, Sekellick and Marcus *Methods in Enzymol.*, 19:115–125 (1986). It has been shown herein that the expression of the isolated gene yields functional chicken interferon.

The amino acid sequence encoding the signal region and mature chicken interferon protein has been deduced (SEQ ID NO: 1). The mature protein has the amino acid sequence of SEQ ID NO: 2. Chicken interferon is a 20–30 KD glycosylated protein which is acid stable. The nonglycosylated molecule is an 18 KD protein. Directed mutation at the 4 potential N-glycosylation sites could lead to chicken interferon molecules with varying degrees of stability and enhanced biological activity. The 6 cysteine residues in the chicken interferon molecule provide the possibility of altering the number of potential disulfide bonds and, hence, stability properties of the molecule, as has been reported for mammalian interferons. Day et al., *Journal of Interferon Research*, 12:139–143 (1992). In this context, the acid labile form of chicken interferon reported by Yoshida and Marcus (*Journal of Interferon Research*, 19:461–468 (1990)), may reflect such transient changes.

Using chicken IFN cDNA as a hybridization probe, we cloned a 2.7 kb HinDIII fragment of genomic duck DNA that contains a gene for duck IFN. It has an open reading frame which is believed to encode a protein of 191 amino acids, including a signal peptide of 30 residues. Like the genes for mammalian type I IFN's and chicken interferon, the duck IFN gene is intronless. The duck IFN shows about 50% sequence identity to chicken IFN, has six conserved cysteine residues and two potential glycosylation sites. Northern blot analysis revealed that duck IFN mRNA is about 900 nucleotides long. It is not detectable in cultured duck embryo cells without induction but accumulates to high levels in cells treated with UV-inactivated Newcastle disease virus.

In mammals, four families of type I interferon genes have been described, (e.g. interferon-alpha, beta, -omega and -tau) and one family of type II interferon (e.g. interferon-gamma). Southern analysis of genomic chicken DNA that have been carried out using probes described herein for chicken interferon indicates there may be only one chicken interferon gene. At the amino acid level, the chicken interferon gene shares only about 22% homology with all other type I mammalian interferons, i.e., interferons -alpha, -beta, -omega and -tau, and less than 3% homology with the type II mammalian interferon, i.e., interferon -gamma. It has been determined herein that chicken interferon is unusual in its content of 6 cysteine residues and 4 potential N-glycosylation sites. Because of its ancestral origin, the chicken interferon gene can be useful in detecting and isolating interferon genes of other nonmammalian species, for example, avian, fish and reptiles.

Several in vitro studies have demonstrated that ChIFN is effective as an antiviral agent against avian viruses in chicken cells, and have implicated IFN as protective agent when chickens were treated with an inducer of IFN and challenged with avian influenza virus (Portnoy and Merigan, J. *Infectious Diseases*, 124:545–552 (1971). Avian influenza virus was found to be sensitive to ChIFN, comparable in degree to vesicular stomatitis virus. Glycosylated recombinant ChIFN (glyco rChIFN),obtained as described below, is active against avian influenza virus (strain A/turkey/Ont/7732/66-H5N9), vesicular stomatitis virus and Infectious Bursal Virus in vitro.

Also, ChIFN has been shown to be biologically active, e.g., produce an antiviral effect, in the cells of other avian species, e.g., turkey, quail, partridge and Guinea fowl (Moehring and Steinebring, *Nature*, 226:360–361 (1970)).

Mammalian interferons have been engineered genetically to display more desirable traits, for example, altered host range and enhanced specific activity. Day et al., Ibid. Thus, using similar techniques it may be possible that the chicken interferon gene could be manipulated similarly.

Recombinant avian, such as duck or chicken, interferon can then be administered to fowl, preferably chickens and exotic birds, in an amount effective to treat or prevent viral and/or parasitic infections and/or to enhance the immune system (such as to augment the action of vaccines). Examples of avian viruses for which chicken interferon could be used to treat/prevent diseases caused thereby include but are not limited to orthomyxovirus (eg., influenza); paramyxovirus (eg., Newcastle disease virus); coronavirus (eg., infectious bronchitis); hepadnavirus (eg., hepatitis); poxvirus (eg., fowl pox); adenovirus (eg., adenovirus); retrovirus (eg., leukosis virus); herpesvirus (eg., Marek's disease, and Laryngotracheitis virus). Rous-sarcoma virus and Infectious Bursal virus infections can also be prevented or treated with the recombinant interferons of the present invention. Parasitic infection such as that caused by Eimeria or other parasites which are controllable by interferon can also be treated/prevented using the recombinant interferon of this invention.

Interferons, such as chicken interferon, are a potent inducer of the Mx gene (which contains an IFN-stimulated Response Element (ISRE)), which encodes a family of GTP-binding proteins (Pavlovic and Stackeli, *J. Interferon Res.*, 11:215–219 (1991)). When stimulated by the action of interferon, the intracellular Mx gene product renders cells refractory to infection by avian influenza virus (Garer et al., *Virology*, 180:754–762 (1991)). Thus, administration of a recombination-interferon, such as glyco-rChIFN can prevent viral infection, such as by avian influenza virus.

The interferon can be formulated into a veterinary preparation, for example, in semisolid or liquid form, which contains the recombinant chicken interferon, as an active ingredient, in admixture with suitable organic or inorganic carriers or excipients. The active ingredient may be compounded, for example, with the usual non-toxic, veterinary carriers for solutions, emulsions, suspensions and any other form suitable for use. The carriers which can be used include albumin, water (such as, drinking water), glucose, lactose, gum acacia, gelatin, mannitol, starch paste, saline, and other carriers suitable for use in manufacturing preparations. In addition auxiliary, stabilizing and thickening agents may be used.

The composition is administered to the fowl by an effective delivery method. Examples of delivery methods include genetic immunization as described above, intraperitoneal, intravenous, intratracheal, respiratory inhalation, such as aerosolization and per os. The dosage of effective amount of chicken interferon will depend upon the age and condition of the fowl. A daily dose typically is $2–10\times10^4$ units/kg, such as $5\times10^4$ units/kg. Because the invention makes it possible to produce large amounts of biologically active rChIFN, doses of ChIFN which were heretoforth unattainable can be administered. See Sekellick and Marcus (1986), Ibid. for standard techniques for determining the unit measure for interferon.

An alternative mode of administration is to produce a transgenic plant, such as corn, which expresses the recombinant interferon. This plant, or a portion thereof (such as corn kernels), can then be fed to the fowl.

An alternative method for preventing and/or treating viral and parasitic infection is to produce transgenic fowl where the fowl harbors an inducible gene encoding interferon endogenous to that fowl. The method of making the transgenic fowl includes the steps of introducing and incorporating recombinant DNA comprising a nucleotide sequence coding for avian interferon at an embryonic stage, preferably in the sperm, ovum, zygote or embryo, of a fowl and incubating said embryonic stage under conditions necessary for development of the fowl. Preferably, the fowl is a chicken. For example, the transgenic fowl can be prepared by incorporating the cDNA, preferably with a predetermined promoter, into a eukaryotic expression vector, for example, plasmid pcDNA3 (Invitrogen). The thus obtained plasmid DNA can then be incorporated into the desired fowl by methods generally recognized in the art. Simkiss, *Comparative Biochemistry and Physiology*, 104A:411–417, (1993); Ono et al., *Developmental Biology*, 161:126–130, (1994). Expression of the interferon in the fowl can protect the fowl from viral and/or parasitic disease.

The chicken interferon gene, generally, is operably placed behind promoters that will respond to stimuli other than the endogenous promoter for the gene. Double stranded (DS) RNA can be used to stimulate the promoter (Marcus, "In Interferon 5", Edition I, Gresser, Academic Press, pp. 115–180, 1983). A chicken metallothionein promoter can also be used (Fernando and Andrews, *Gene*, 81:177–183 (1989)), so that the cells or chickens containing this construct would respond to metal ions, such as $Cd^{++}$ or $Zn^{++}$, and produce interferon transiently, as desired.

The metal ions can be administered by any effective means, including orally or parenterally. The most preferred embodiment is oral administration. The metallic ions can be formulated in any effective composition. Suitable carriers include those described above. For example, the metallic ions can be incorporated into the fowl's feed, where ingestion of the metallic ion induces the metallothionein promoter. The effective dosage of the metallic ions can be readily determined by the skilled artisan, and depend upon the age and condition of the fowl.

The invention will be used to establish transgenic chickens that either constitutively express the chicken interferon gene, so that the chicken displays resistance to a broad spectrum of viral infections comparable to that observed in vitro, or transiently express chicken interferon as required to prevent or combat virus infection. Transiently expressed interferon is preferred because constitutive expression results in levels of interferon that might be deleterious to embryonic development. See Muller et al., *Gene*, 121:263–270 (1992) in which the early expression of the Mx'1 gene was shown to be deleterious in transgenic pigs. In activating the interferon gene system, this approach has the advantage of bringing the interferon system in to play only when required, as during outbreak of a viral disease, and not during critical developmental stages in the establishment of the transgenic chickens.

Chicken interferon expressed in this manner has the added advantage of also activating the Mx system, as it does naturally, and may render the chickens resistant to avian influenza virus as well. Avian influenza and other avian viruses can decimate flocks, and chickens that were intrinsically resistant to virus or could be activated to resistance by simply manipulating the feed would be of great commercial value. The chicken industry is a multibillion dollar industry.

Any effective method for incorporating the cDNA plasmid into the fowl can be used. Examples of such methods include microinjection, electroporation, sperm transfection, liposome fusion, and microprojectile bombardment. The desired gene can also be introduced into sperm cells by the Cornell particle gun. Microprojectile bombardment employing the Cornell particle gun was developed to deliver desired genetic constructs into cells by firing DNA-coated inert microparticles, such as tungsten into the cells. Hough and Foote, "The Effect of the Cornell Particle Gun on Bull and Rabbit Spermatatozoa", *Abs. Biol. Reprod. Suppl.* 1 42:65, (1990); U.S. Pat. No. 5,100,792, Sanford et al., issued Mar. 31, 1992, incorporated by reference herein.

Another method for producing transgenic chickens is using "one round" retroviral vectors. See Salter, et al., Transgenic Chickens: Insertion of Retroviral Genes into the Chicken Germ Line, *Virology*, 157:236–240 (1987), for example. It is reported that insertion of foreign DNA in early chicken embryos occurred where the DNA was injected into the yolk near the embryo in a newly laid fertile egg. The procedure employed is described in Salter et al., *Poult. Sci.*, 65:1445–1458 (1986), which is incorporated herein by reference.

It is particularly advantageous to modify the retroviral vector to improve their efficiency and reduce pathogenicity. One method which may be employed is the deletion of at least one replication gene of the retroviral vector. Crittenden and Salter, Poc. UCLA Symp., Transgenic Models in Med and Agr., pp 73–87, 1990; Salter and Crittenden, *Theor. Appl. Genetics*, 77:457–461 (1989); Crittenden, Salter and Federspiel, *Theor. Appl. Genetics*, 77:505–515, 1989; Salter and Crittenden, "Proc. Discoveries in Antisense Nucleic Acids", pp 95–110, (1989); Salter et al., *Virology*, 157:236–240, 1987; Crittenden et al., *J. Virol.*, 61:772–775, 1987; Crittenden, *Poultry Sci.*, 65:1468–1473 (1986); Crittenden, *Avian Dis.*, 30:43–46 (1986); Hughes, *Poultry Sci.*, 65:1459–1467 (1986); Salter et al., *Poultry Sci.*, 65:1445–1458 (1986); Crittenden and Salter, *Canadian J. of Animal Science*, 65:553–562 (1985); Simkiss, *Comparative Biochemistry and Physiology*, 104A:411–417, (1993); and Ono et al., *Developmental Biology*, 161:126–130, (1994).

Production of a successful transgenic chicken with non-replicating vectors has been described. Shuman, *J. of Dairy Sci.*, 72(suppl 1):61 (1989); Lee, M. R., Ph.D. Thesis, North Carolina State University, (1989); Shuman et al., *Poultry Sci.*, 67:136 (1988). None of these transgenic chickens contain the chicken interferon cDNA described herein.

In the method of this invention the DNA construct, discussed above, optionally with a suitable promoter, is impregnated in or coated on an inert microparticle. The DNA coated or impregnated microparticle is then delivered into the appropriate cell, including the sperm, ovum, zygote or embryo. Because sperm cells are natural vectors, it is preferred that the DNA coated microparticle is delivered into the sperm. It is preferred that the Cornell particle gun be employed in the delivery of the microparticle to the cell. However, any mode of effective delivery can be employed, including those described in the Sanford patent. While some loss of sperm motility may be experienced, application of a vacuum and addition of ATP may recapture some or all motility. Preferred ATP concentrations are 0.05–1.0 mM ATP.

Newly hatched chicks can be screened for the chicken interferon gene by exposing leukocytes from blood sample to $Zn^{++}$ or $Cd^{++}$ ions to induce the metallothionein promoter driven ChIFN gene.

In another embodiment, the ability of recombinant interferon to activate the Mx gene system is exploited. for example, the Mx gene promoter is operably placed next to a heterologous gene for which expression in a host cell is desirable. The host cell (such as an avian or chicken cell) is transfected with the Mx gene promoter and the heterologous gene. The expression of the heterologous gene is then induced by exposing the cell to the recombinant interferon.

The cDNA probe and/or the chicken interferon gene and/or any effective fragment thereof can be used as a probe to isolate the interferon gene of other avian species, fish or reptile. The method to be employed is substantially the same used and described above for isolating the chicken interferon gene.

The interferon gene so isolated can then be used, in the manner described above, for the preparation of the recombinant interferon protein or for the preparation of a transgenic animal. The recombinant interferon protein can be administered to an appropriate avian, fish or reptile in the manner described above. The administration of interferon to fish can also be accomplished, for example, by adding the interferon to the aqueous environment. The interferon may be absorbed through the gills of the fish.

Interferon can be injected into eggs to provide protection to the embryo using known techniques.

The invention will be further illustrated by the following exemplification:

EXEMPLIFICATION

MATERIALS AND METHODS

Cells and Media: Monolayers of primary chick embryo cells were prepared from 10-day-old chick embryos as previously described (Sekellick and Marcus, *Methods Enzymol.*, 119:115–125, (1986); Sekellick, Biggers and Marcus, *In Vitro Cell Dev. Biol.*, 26:997–1003 (1990)). Cells were aged in vitro without a medium change for the periods of time indicated, usually 8–10 days, to enhance their IFN-inducing capacity (Sekellick and Marcus, (1986); Sekellick, Biggers and Marcus, (1990).

Source of Viruses, Preparation and Assay: The origin, growth and source of avian reovirus as well as various strains of wild-type VSV IN have been described (Winship and Marcus, *J. Interferon Res.*, 1:155–167 (1980); Sekellick and Marcus, *J. Gen. Virol.*, 70:405–415 (1989); Sekellick and Marcus, *Virology*, 95:36–47 (1979); Marcus, Sekellick & Nichol (1992); Marcus et al., *J. Interferon Res.*, 13:547 (1993)). Plaque assays, stock amplification and UV radiation of avian reovirus were performed as previously described using primary chick embryo cells as host (Winship and Marcus, (1980)). VSV preparations were grown and plaqued in GMK-Vero cells as described previously (Sekellick and Marcus, (1989)).

IFN Induction and Assay: Details for the procedures used to induce and assay acid stable IFN in aged primary chick embryo cells have been described (Sekellick and Marcus (1986); Sekellick, Biggers and Marcus, (1990); Yoshida and Marcus, *J. Interferon Research*, 10:461–468, (1990)). UV-irradiated avian reovirus was used to infect primary chick embryo cells at a multiplicity of infection of 5 as described previously (Winship and Marcus, (1980)) in order to induce IFN maximally.

RNA Purification: Total cellular RNA was obtained from UV-irradiated-avian reovirus infected primary chick embryo cells at various times post infection. Cells were lysed with SDS/EDTA and total RNA extracted with water-saturated acid phenol followed by ethanol precipitation (Maniatis, Fritsch & Sambrook, *Molecular Cloning: A Laboratory Manual* (2nd Ed.), Cold Spring Harbor Laboratory Press (1989)). RNA extracted in this manner served as template in a PCR reaction or for Northern blot analysis.

Oligonucleotide Synthesis: Known mammalian IFN-α/β and amino acid sequences were obtained by using the Wisconsin Sequence Analysis Package, Verson 7, from Genetics Computer Group (Madison, Wis.) and were aligned to minimize gaps and maximize homology. Regions exhibiting high homology near the carboxyl end and middle of the mature protein were examined in detail at the amino acid level, and two probes were constructed based on nucleotide sequences from these regions. Nucleotide sequences were derived from amino acid sequences, favoring codon preferences observed for known chicken genes, while substituting two or more nucleotides at degenerate positions. For PCR, the "downstream" primer was antisense for cDNA synthesis and the "upstream" primer was sense for amplification of the cDNA with the "downstream primer". Sense and anti-sense degenerate PCR primers corresponded to nucleotide positions 307–338 and 556–575, respectively (SEQ ID NO: 1). The sense primer was a 32-mer consisting of the sequence 5'-TTGGCCATCTATGAGATGCTCCAGMANATHTT-3' (SEQ ID NO: 4). The anti-sense primer was a 20-mer consisting of the sequence 5'-CGGACCACTGTCCANGCRCA-3' (SEQ ID NO: 5).

Polymerase Chain Reaction (PCR): RNA PCR was performed according to the protocol provided with the Perkin Elmer-Cetus Geneamp RNA PCR kit. Briefly, one microgram of total RNA isolated from primary chick embryo cells that were induced to produce interferon was used in a 20 μl reverse transcription reaction using the downstream primer for cDNA synthesis. The reaction was carried out at 42° C. for 15 minutes and then at 99° C. for 5 minutes to inactivate the reverse transcriptase. After cooling to 5° C., reaction components were added to give a 100 μl volume with both primers now present at a concentration of 0.5 μM. PCR was carried out for 35 cycles of 95° C. for 1 minute, 37° C. for 1 minute and 72° C. for 1 minute.

Purification of PCR Products: PCR products were ethanol precipitated, redissolved in water, and run out on a 3% Nusieve GTG agarose (FMC) gel. The band of the expected size was cut from the gel, melted, and diluted 1:10 with sterile water. A 10 μl volume of this solution was used in another PCR reaction to amplify even more of the fragment so a sufficient amount was available for cloning. Reaction conditions were performed as before except the annealing was performed at 50° C. PCR products were again gel purified except the excised bands were purified from the agarose by spinning in a microfuge through Costar spin-X centrifuge filter units at 4° C. The samples were then extracted with sec-butanol to remove ethidium bromide, quantitated, ethanol precipitated and redissolved in sterile water.

Synthesis of the cDNA Fragment: The phagemid pbluescript KS(−) was cut with Eco RV to produce a blunt end and also cut with Eag I to produce a 3' overhang on the other end. The purified PCR product contained a single restriction site for Eae I toward the 5' end of the upstream primer which produced a 3' end overhang complementary to that produced by Eag I. The fragment was ligated into pBluescript under conditions favoring blunt end ligations with a molar ratio of insert:vector of 10:1. Recombinant plasmids were transformed into XL1-Blue *E. Coli.* Positive colonies were identified using blue/white colony selection. Recombinants were then verified by restriction digests that produced inserts of the expected size. A clone containing a 269-base insert (designated pCh269) was selected for use in subsequent studies.

DNA Sequencing of the Cloned PCR Fragment: Double-stranded DNA sequencing was performed using TAQuence Version 2.0 from USB. Plasmid was prepared from 500 ml cultures by the alkaline lysis method. Contaminating RNA was removed by lithium chloride precipitation and RNase treatment followed by organic extraction and ethanol precipitation. Plasmid was heat-denatured and flash frozen in dry ice and ethanol prior to performing sequencing reactions. Completed reactions were than analyzed on a 7% Long Ranger (J. T. Baker) polyacrylamide gel using sequencing reactions from both strands of the plasmid insert.

cDNA Cloning: Using aged primary chick embryo cells infected with UV-AVR, conditions known to produce high yields of interferon, total RNA was isolated from cells at about 8 hours post infection as described above. Poly(A)$^+$ RNA was isolated from oligo(dT)-cellulose spun columns supplied with a Pharmacia mRNA Purification Kit. cDNA was synthesized from this poly(A)$^+$ RNA and cloned into Not I-Sal I-cut plasmid pSPORT I using a Superscript Plasmid System (Gibco/BRL). Plasmid was electroporated into ElectroMAX DH10B (Gibco/BRL) cells using the "Electroporator" electroporating apparatus from Invitrogen. Clones were screened using biotinylated-PCR product prepared from pCh269 template and hybridized to DNA from colony lifts which were UV-crosslinked to MSI nylon membranes (82 mm diameter) and detected with the Colony Images Non-Isotopic Colony/Plaque Screening Kit (USB).

DNA Sequencing of cDNA Clones: Plasmids were isolated using a standard alkaline lysis method followed by ammonium acetate precipitation (for 10 ml cultures) or lithium chloride precipitation (for 500 ml cultures). This was followed by RNase treatment to remove residual contaminating bacterial RNA. The plasmids were then sequenced using the Pharmacia AutoRead Sequencing Kit for double-stranded templates with T7 and SP6 fluorescein labelled primers (supplied by the Biotechnology Center, Univ. of CT). Following termination, sequencing reactions were analyzed on the Pharmacia Automated Laser Fluorescent A.L.F. DNA sequencer using a 6% polyacrylamide gel.

Northern Blot Analysis: RNA samples were run out for 3 hours on a 1% agarose gel containing 2.2M formaldehyde and transferred to a nylon membrane by capillary elution in 10× SSC. RNA was cross-linked to the dry membrane with 254 nm UV (0.15 J/cm$^2$). The Gibco/BRL Photogene protocol was followed for probe hybridization and nonradioactive nucleic acid detection. Hybridization solutions contained 50% formamide and reactions were performed at 42° C. Stringency washes were performed under moderate conditions using 1% SSC and 1% (w/v) SDS at 50° C. for 30 minutes. Membranes were exposed to Kodak XAR-5 film usually for 2–4 hours to obtain a signal of sufficient intensity.

Biological Activity of DChl32 Gene Product: pCh132 DNA was linearized with Hind III and used as template in an in vitro transcription reaction using a mCAP kit (Stratagene, La Jolla, Calif.) to prepare capped mRNA with T7 RNA polymerase. Following DNase digestion, the RNA product was purified by phenol extraction and ethanol precipitation. RNA was resuspended in TE buffer for use.

pCh132 mRNA was transfected into mouse L(Y)-Clone 40 cells using Lipofectin Reagent (Gibco/BRL) as recommended by the manufacturer. Monolayers of cells in 60 mm dishes were washed 4 times with serum-free minimal essential medium (MEM) prior to addition of the Lipofectin-mRNA complex in 2 ml of serum-free MEM. Cells were incubated at 37° C. for 4–20 hours. Supernatants were stored at −20° C. prior to assay for IFN on primary chick embryo cells as described. Sekellick and Marcus, *Methods in Enzymol.*, 119:115–125 (1986).

In a separate experiment, supernatant medium from mouse L(Y)-Clone 40 cells transfected with 5 μg of RNA and collected 4 hours post transfection as described above, contained 26 units/ml of antiviral activity when tested on primary chick embryo cells. This activity was neutralized completely by incubation with a 1:25 dilution of a monoclonal antibody to ChIFN sufficient to neutralize 40–160 international units of ChIFN (Masayoshi Kohase, personal communication).

Figure 1:
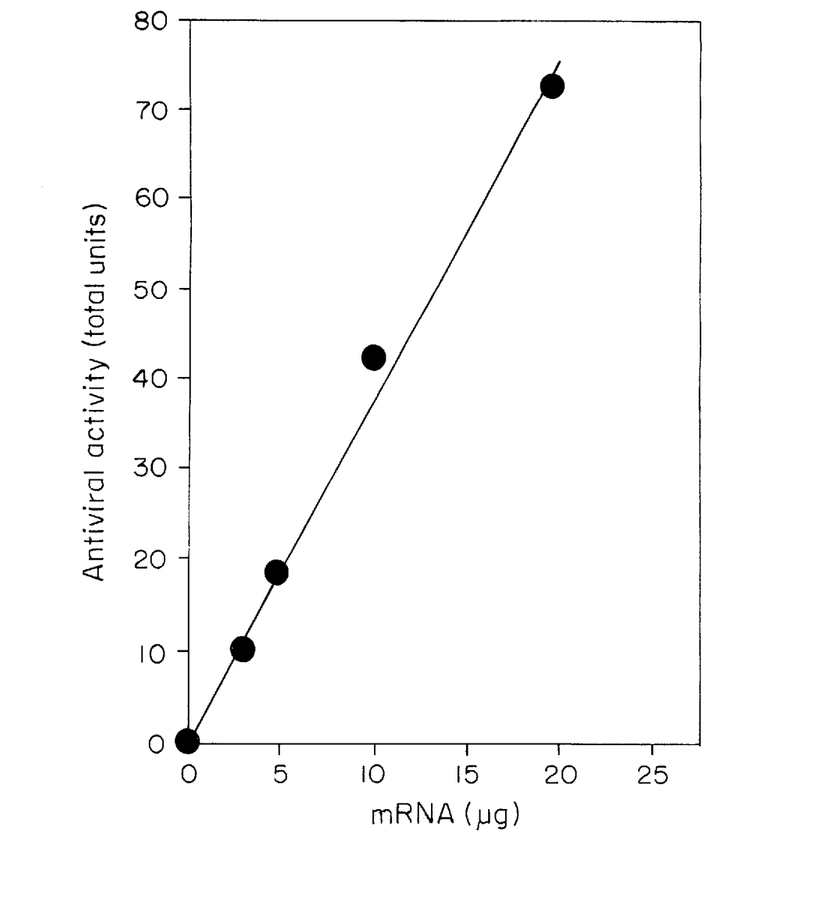
The FIGURE is a graph showing the relationship of antiviral activity produced by mouse L(Y) cells 20 hours after lipofectin-mediated transfection of chick embryo cells with mRNA transcribed from pCh132 DNA. The activity was neutralized completely with a monoclonal antibody to ChIFN. A preparation of mouse IFN which assayed at 65,000 units/ml on mouse L(Y) cells showed no antiviral activity on chick embryo cells.

Biological expression of the ChIFN gene in Mouse L(Y) cells: Messenger RNA prepared in vitro using pCh132 DNA as template was transfected into mouse L(Y) cells and the medium tested for antiviral activity in a standard assay on chicken cells (Sekellick and Marcus, *Methods in Enzymol.*, 119:115–125, 1986) carried out in the presence or absence of monoclonal antibody specific for ChIFN. (Kohase et al., *J. Interferon Res.*, 13:S93, 1993) The highest level of antiviral activity released into the medium bathing the mouse L(Y) cells was observed 4 hours post-transfection, and decreased to one-third by 8 hours, after which time it remained constant for at least 20 hours. Cell extracts contained about 10% of the antiviral activity released by the cells. The figure shows that the activity recovered from transfected mouse L(Y) cells induced an antiviral effect in chicken cells that was proportional to the amount of mRNA added in the lipofectin-mediated transfection. This activity was neutralized by both polyclonal and monoclonal antibody specific for ChIFN. Mouse IFN was not active on chick cells, and hence the antiviral effect could not be attributed to IFN endogenously induced during the transfection process. This latter control was necessary since some plasmid preparations may be contaminated with double-stranded (ds)RNA, a potent IFN inducer. Marcus and Sekellick, *Nature*, 266:815–819 (1977).

Biological expression of glycosylated rChIFN in human WISH cells and COS-1 cells: DNA was prepared from the eukaryotic expression plasmid pcDNA3 (purchased from Invitrogen, San Diego, Calif.) and from clone pCh132. Both preparations of plasmid DNA were cut with restriction enzymes Eco R1 and Not 1. The linearized pcDNA3 plasmid was purified using phenol/chloroform extraction followed by ethanol precipitation and the DNA was resuspended in TE buffer. The DNA products that resulted from restricting the plasmid pCh132 were separated on a It agarose gel and the DNA band containing the insert with the coding sequence for chicken interferon was cut out of the gel. The insert was purified from the agarose using a Spin-X column (Costar) followed by butanol extraction and ethanol precipitation. The insert DNA was resuspended in TE buffer. Ligation of the insert into the pcDNA3 vector was carried out using T4 DNA ligase at 16° C. with an insert to vector ratio of 10:1.

Products of this ligation reaction were used to transform DH5a cells. Transformed cells were isolated using ampicillin selection. Ten colonies were selected, DNA prepared and subjected to restriction digestion, and the products analyzed on an agarose gel. Five of the ten clones contained plasmids with inserts of a size consistent with that expected for the insert derived from pCh132.

DNA preparations from the positive clones (designated A1, A2, A3, A7, A10) were used to transfect COS-1 cells (obtained from the ATCC, Rockville, Md.) and WISH cells plated in 60 mm dishes. Cells were washed four times with serum free/antibiotic free medium ($CO_2$-Independent medium [Gibco/BRL] for COS-1; MEM for WISH). In separate reactions, approximately 2–4 gg of DNA from each of the five clones was combined with 25 μl of Lipofectin Reagent (Gibco/BRL) and incubated as described by the manufacturer. The Lipofectin-DNA complex was added to cells (COS-1 and WISH) in serum free/antibiotic free medium. Transfected cells were incubated at 37.5° C. and medium collected at 12, 24, 28 and 72 hours. At 72 hours post-transfection, cells were trypsinized and pooled (i.e., the five cultures of COS-1 cells transfected with the five clones were pooled together and the five cultures of WISH cells tranfected with the five clones were pooled together). Transfected COS-1 cells were replated into DME with 10% FBS and G418 at 400 μg/ml. Transfected WISH cells were replated into MEM with 10% FBS and G418 at 1000 μg/ml. Assay of the supernatant medium (on primary chick embryo cells) collected from 12 to 72 hours from the transfected cells showed that all five clones (A1, A2, A3, A7, A10) produced significant amounts of antiviral activity from both the COS-1 and WISH cells.

Transfected cells, surviving the initial G418 selection, were maintained with medium changes (without G418) and/or passage until stable cultures developed. In the case of the transfected COS cells surviving G418 drug treatment, cells were pooled into a single well of a 24-well tray and transferred to a 60 mm dish about 5 weeks after the initial transfection procedure. Medium (5 ml) collected 10 days after seeding cells into one 60 mm dish was assayed for chicken interferon and found to contain approximately $1 \times 10^6$ units per ml or a total of $5 \times 10^6$ units.

Antiviral Action of Glyco-rChIFN: As noted in footnote [(2)] of Table 1, Vesicular stomatitis virus (VSV) was used as an international standard to define 1 plaque-reduction-50% ($PR_{50}$) unit of ChIFN. The $PR_{50}$ is a well-known, standard biological assay to measure the activity of IFN (*Interferon and Interferon Inducers*, Revised Edition edited by N. B. Finter, North Holland/American Elsevier Press, pages 139–142, 1973).

Briefly, each virus to be tested is plaque assayed by standard and well-known procedures (R. Dulbecco, 1952), first on susceptible chick embryo cells in the absence of IFN to give the control plaque titer, and then in the presence of different dilutions of the IFN being tested. The reciprocal of the dilution of IFN that reduces the control plaque titer by 50 percent contains, by definition, 1 $PR_{50}$ unit of IFN. In Table 1, a value of 1 under "Relative sensitivity to glyco-rCHIFN [1] means that the virus displays the same sensitivity to IFN as does the standard VSV. VSV is considered very sensitive to the action of IFN, therefore, avian influenza virus which generates a value of 1 is as sensitive as VSV to the action of IFN. Infectious bursal virus produced a value of 2, and therefore that virus requires twice as much IFN to reduce its plaque forming capacity by 50%.

TABLE 1

Antiviral Action of Glyco-rChIFN[1]

| Virus | Relative Sensitivity to Glyco-rChIFN[2] |
|---|---|
| Vesicular stomatitis (VSV-IN-HR) | 1[2] |
| Avian influenza (H5N9) | 1 |
| Infectious bursal disease | 2 |
| Newcastle disease (NDV) | 7 |
| Marek's disease[3] | 6 |

[1]Prepared from COS-1 cells transfected with pCh132A3. This construct contains the ChIFN gene, the invention, driven by a CMV (cytomegalovirus) promoter. This preparation of glyco-rChIFN assays at $1.5 \times 10^6$ VSV $PR_{50}$ units/ml.

TABLE 1-continued

Antiviral Action of Glyco-rChIFN[1]

| Virus | Relative Sensitivity to Glyco-rChIFN[2] |
|---|---|

[2]VSV is used as an international standard to define 1 $PR_{50}$ unit of ChIFN. By definition it registers a sensitivity = 1. A unit of IFN is the amount (reciprocal of the dilution) of IFN that will reduce the plaque titer of VSV by 50% when assayed on a monolayer of chick embryo cells. One International standard unit = 1 Laboratory unit (Sekellick and Marcus, Methods in Enzymology, 119:115–125, (1986). A value of 1 means that the test virus and VSV are equally sensitive to the action of rChIFN. VSV is considered highly sensitive to the action of IFN. Values <1 mean the test virus is more sensitive, and values >1 mean it is less sensitive than VSV. Thus, Newcastle disease virus requires 7-times more IFN than VSV to register a 50% reduction in plaque number on chicken cells.
[3]The antiviral effect of ChIFN against this tumor-producing herpesvirus was measured by the degree of suppression of MDV antigen expression scored by immunofluoresence. Fifty percent suppression was obtained with about 6 units of native ChIFN.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims:

We claim:

1. A method of treating viral and/or parasitic infection of a fowl by orally administering an effective amount of avian interferon to the fowl.

2. A method of claim 1, wherein the avian interferon is chicken interferon.

3. A method of claim 1, wherein said fowl is an exotic bird.

4. A method of claim 1, wherein said fowl is a chicken.

5. A method of preventing viral and/or parasitic infection of a fowl by orally administering an effective amount of avian interferon to the fowl.

6. A method of claim 5, wherein the avian interferon is chicken interferon.

7. A method of claim 5, wherein said fowl is an exotic bird.

8. A method of claim 5, wherein said fowl is a chicken.

9. A method of treating viral and/or parasitic infection in a fowl by orally administering to the fowl a therapeutically effective amount of an avian interferon essentially free of other avian proteins, wherein said avian interferon is encoded by a DNA molecule wherein the DNA comprises a sequence selected from the group consisting of:

a) nucleotides 148 through 633 of SEQ ID NO. 1; and b) the sequence of a DNA molecule isolated from an avian DNA library, wherein said DNA molecule encodes an avian type I interferon mature protein and wherein said DNA molecule hybridizes under conditions of moderate stringency to a probe having the sequence of the full length complement of the coding sequence shown in SEQ ID NO: 1.

10. A method of preventing viral and/or parasitic infection in a fowl by oral administering to the fowl a therapeutically effective amount of an avian interferon essentially free of other avian proteins, wherein said avian interferon is encoded by a DNA molecule wherein the DNA comprises a sequence selected from the group consisting of:

a) nucleotides 148 through 633 of SEQ ID NO: 1; and b) the sequence of a DNA molecule isolated from an avian DNA library, wherein said DNA molecule encodes an avian type I interferon mature protein and wherein said DNA molecule hybridizes under conditions of moderate stringency to a probe having the sequence of the fill length complement of the coding sequence shown in SEQ ID NO: 1.

11. A method of treating viral and/or parasitic infection of a fowl by orally administering an effective amount of avian interferon to the fowl wherein said avian interferon is encoded by a DNA molecule wherein said DNA has a sequence selected foom the group consisting of:

a) nucleotides 148 through 633 of SEQ ID NO: 1; and b) the sequence of a DNA molecule isolated from an avian DNA library, wherein said DNA molecule encodes an avian type I interferon mature protein and wherein said DNA molecule hybridizes under conditions of moderate stringency to a probe having the sequence of the full length complement of the coding sequence shown in SEQ ID NO: 1.

12. A method of preventing viral and/or parasitic infection of a fowl by orally administering an effective amount of avian interferon to the fowl wherein said avian interferon is encoded by a DNA molecule wherein said DNA has a sequence selected from the group consisting of:

a) nucleotides 148 through 633 of SEQ ID NO: 1, and b) the sequence of a DNA molecule isolated from an avian DNA library, wherein said DNA molecule encodes an avian type I interferon mature protein and wherein said DNA molecule hybridizes under conditions of moderate stringency to a probe having the sequence of the full length complement of the coding sequence shown in SEQ ID NO: 1.

13. A method of treating viral and/or parasitic infection in a fowl by orally administering a therapeutically effective amount of chicken interferon to the fowl wherein said chicken interferon is essentially free of other chicken proteins and has the amino acid sequence of SEQ ID NO: 2.

14. A method of claim 13 wherein said fowl is an exotic bird.

15. A method of claim 13 wherein said fowl is a chicken.

16. A method of preventing viral and/or parasitic infection in a fowl by orally administering a therapeutically effective amount of chicken interferon to the fowl wherein said chicken interferon is essentially free of other chicken proteins and has the amino acid sequence of SEQ ID NO. 2.

17. A method of claim 16 wherein said fowl is an exotic bird.

18. A method of claim 16 wherein said fowl is a chicken.

* * * * *